United States Patent [19]
Löser et al.

[11] Patent Number: 5,902,830
[45] Date of Patent: May 11, 1999

[54] USE OF DROLOXIFENE FOR THE TREATMENT OF CARDIOVASCULAR DISEASE

[75] Inventors: Roland Löser, Feldafing; Michael Schliack, Münich, both of Germany; David D. Thompson, Gales Ferry, Conn.

[73] Assignee: Pfizer Inc., New York, N.Y.

[21] Appl. No.: 09/048,568

[22] Filed: Mar. 26, 1998

Related U.S. Application Data

[60] Division of application No. 08/605,131, Mar. 13, 1996, filed as application No. PCT/IB95/00403, May 26, 1995, which is a continuation-in-part of application No. 08/276,969, Jul. 19, 1994, Pat. No. 5,441,986.

[51] Int. Cl.[6] .................................................. A61K 31/135
[52] U.S. Cl. ............................................................. 514/648
[58] Field of Search ................................................ 514/648

[56] References Cited

U.S. PATENT DOCUMENTS

| | | |
|---|---|---|
| 5,047,431 | 9/1991 | Schickaneder et al. ................. 514/648 |
| 5,254,594 | 10/1993 | Niikura et al. ............................ 514/648 |
| 5,384,332 | 1/1995 | Fontana .................................... 514/648 |
| 5,426,123 | 6/1995 | Fontana .................................... 514/648 |
| 5,455,275 | 10/1995 | Fontana .................................... 514/648 |

OTHER PUBLICATIONS

Gill–Sharma, M.K., et al., "Effects of Tamoxifen on the Fertility of Male Rats", Journal of Reproduction and Fertility 99, 395–402 (1993).

Schneider, M. R. et al., "Effect of zindoxifens on experimental prostatic tumours of the rat", J Cancer Res Clin Oncol 117:33–36 (1991).

Faulkner, et al., "Regional and Total Body Bone Mineral Content, Bone Mineral Density, and Total Body Tissue Composition in Children 8–16 Years of Age" Calcified tissue 53:7–12 (1993).

Jones, Robert C., "The Effect of a Luteininzing Hormone Releasing Hormone (LRH) Agonist (Wy–40,972), Levonorgestrel, Danazol and Ovariectomy on Experimental Endometriosis in the Rat" Acta Endocrinologica 106, 282–8 (1994).

Wiseman, H., "Tamoxifen: New Membrane–Mediated Mechanisms of Action and Therapeutic Advances", Tips, 101–15 (1994).

Wiseman, H., et al., "Droloxifene (3–hydroxytamoxifen) has membrane antioxidant ability: potential relevance to its mechanism of therapeutic action in breast cancer", Cancer Letters, 66 61–68 (1992).

Steinberg, D., et al., "Beyond Cholesterol Modifications of Low–Density Lipoprotein that increase its Atherogenicity", The New England Journal of Medicine, 915–924 (1989).

Wiseman, H., et al., Protective actions of tamoxifen and 4–hydroxytamoxifen against oxidative damage to human low–density lipoproteins: a mechanism accounting for the cardioprotective action of tamoxifen?, Biochem, J. 292 635 (1993).

Pritchard, K., "Summary", Am. J. Clin. Oncol., 14 (Suppl. 2) S62–S63 (1991).

Cypriani, B., et al. "Role of Estrogen Receptors and Anti-estrogen Binding Sites in an Early Effects of Antiestrogens, the Inhibition of Cholesterol Biosynthesis", J. Steriod Biochem., vol. 31, No. 5, 763–771, (1988).

Bruning, P.F., "Droloxifene, A New Anti–estrogen in Postmenopausal Advanced Breast Cancer: Preliminary Results of a Double–blind Dose–finding Phase II Trial", Eur F Cancer, vol. 28A, No. 8/9, 1404–1407 (1992).

Neubauer, B. L., et al., "Endocrine and Antiprostatic Effects of Raloxifene (LY156758) in Male Rats", The Prostate, 23:245–262 (1993).

Wiseman, H., et al., "Tamoxifene Inhibits Lipids Peroxidation in Cardiac Microsomes", Biochemical Pharmacology, vol. 45, No. 9, 1851–1855 (1993).

Love, R. R., "Effects of Tamoxifen on Cardiovascular Risk Factor in Postmenopausal Women", Annals of Internal Medicine, 115, 860–864 (1991).

Schwartz, J. et al., "Clinical Pharmacology of Estrogens: Cardiovascular Actions and Cardioprotective Benefits of Replacement Therapy in Postmenopausal Women", J. Clin. Pharmacol, 35:314–329 (1995).

Di Silverio, F., et al., "Pharmacological combinations in the treatment of benign prostatic hypertrophy", Journal d'Urologie, No. 6, 316–320 (1993).

Bierman, E.L., "Atherosclerosis and other forms of arteriosclerosis", 1106–1110 (1989).

"Raloxifene Hydrochloride EN=090328", Drugs of the Future, vol. 15(7), 762–63 (1990).

*Primary Examiner*—Jerome D. Goldberg
*Attorney, Agent, or Firm*—Peter C. Richardson; Gregg C. Benson; Mervin E. Brokke

[57] ABSTRACT

Use of droloxifene in the treatment of cardiovascular diseases.

1 Claim, No Drawings

USE OF DROLOXIFENE FOR THE TREATMENT OF CARDIOVASCULAR DISEASE

CROSS REFERENCE TO RELATED APPLICATIONS

This is a division of co-pending U.S. application Ser. No. 08/605,131, filed Mar. 13, 1996, allowed; which is the national phase of PCT/IB95/00403 filed May 26, 1995; which is a continuation-in-part of U.S. application Ser. No. 08/276,969, filed Jul. 19, 1994, now U.S. Pat. No. 5,441,986.

FIELD OF THE INVENTION

This invention relates to remedies for cardiovascular diseases comprising, as active ingredient, droloxifene having the chemical structure represented by the following formula,

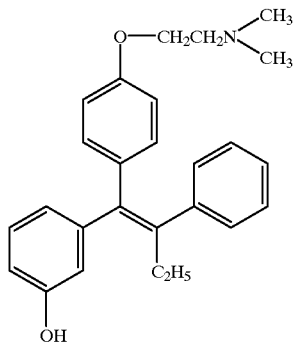

or a pharmaceutically acceptable salt thereof.

BACKGROUND OF THE INVENTION

Droloxifene is a known compound disclosed in U.S. Pat. No. 5,047,431 in which it is disclosed as an anti-tumor agent, particularly for treatment and prevention of cancer of the breast. Droloxifene is also useful for the relief of bone diseases caused by the deficiency of estrogen or the like, which are often observed in women after menopause or those with the ovaries removed. U.S. Pat. No. 5,254,594.

Gill-Sharma, et al., *J. Reproduction and Fertility* (1993) 99, 395, disclose that tamoxifen at 200 and 400 mg/kg/day reduces the weights of the testes and secondary sex organs in male rats.

Neubauer, et al., *The Prostate* 23:245 (1993) teach that raloxifene treatment of male rats produced regression of the ventral prostate.

SUMMARY OF THE INVENTION

This invention provides a method for treating a condition or disease selected from cardiovascular disease or hypercholesterolemia in mammals which comprises administering to said mammal an amount of droloxifene or a pharmaceutically acceptable salt thereof which is effective in treating said condition or disease.

DETAILED DESCRIPTION OF THE INVENTION

The preparation of droloxifene (1-[4'-(2-dimethylaminoethoxy)phenyl]-1-(3'-hydroxyphenyl)-2-phenylbut-1-ene) and pharmaceutically acceptable salts thereof is described in U.S. Pat. No. 5,047,431 which is incorporated herein by reference.

As used in this application, "prostatic disease" means benign prostatic hyperplasia or prostatic carcinoma. "Cardiovascular disease" means hypercholesterolemia and atherosclerosis. "Treating" means curing, alleviating the symptoms of or preventing the onset of a disease or condition.

The remedies for the cardiovascular diseases, hypercholesterolemia and atherosclerosis of this invention comprise, as active ingredient, droloxifene or a salt thereof. The pharmaceutically acceptable salts of droloxifene are salts of non-toxic type commonly used, such as salts with organic acids (e.g., formic, acetic, citric, maleic, tartaric, methanesulfonic, benzenesulfonic or toluenesulfonic acids), inorganic acids (e.g. hydrochloric, hydrobromic, sulfuric or phosphoric acids), and amino acids (e.g., aspartic or glutamic acids). These salts may be prepared by the methods known to chemists of ordinary skill.

The remedies for the diseases and conditions of this invention may be administered to animals including humans orally or parenterally in the conventional form of preparations, such as capsules, microcapsules, tablets, granules, powder, troches, pills, suppositories, injections, suspensions and syrups.

The remedies for the diseases and conditions of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 1 mg to 100 mg in unit dosage for both oral and parenteral administration.

The active ingredient may be usually administered once to four times a day with a unit dosage of 0.25 mg to 100 mg in human patients, but the above dosage may be properly varied depending on the age, body weight and medical condition of the patient and the type of administration. One dose per day is preferred.

The following Examples will serve to illustrate, but do not limit the invention which is defined by the claims.

EXAMPLE 1

Effect on Prostate Weight

Male Sprague-Dawley rats, three months of age were administered by subcutaneous injection either vehicle (10% ethanol in water), estradiol (30 µg/kg), testosterone (1 mg/kg) or droloxifene citrate (10 mg/kg) daily for 14 days (n=6/group). After 14 days the animals were sacrificed, the prostate was removed and the wet prostate weight was determined. Mean weight was determined and statistical significance (p<0.05) was determined compared to the vehicle-treated group using Student's t-test.

Droloxifene citrate at 10 mg/kg/day significantly (P<0.05) decreased prostate weight compared to vehicle. Testosterone had no effect while estrogen at 30 µg/kg significantly reduces prostate weight.

These data showed that droloxifene citrate is useful in the treatment of benign prostatic hypertrophy and prostatic cancer.

EXAMPLE 2

Effect on Total Cholesterol Levels

The effect of the compound of the present invention on plasma levels of total cholesterol was measured in the following way. Blood samples were collected via cardiac puncture from anesthetized female Sprague-Dawley rats 4–6 months of age that were bilaterally ovariectomized and treated with droloxifene citrate (5 mg/kg/day, po) for 28 days or with vehicle for the same time, or sham operated. The blood was placed in tubes containing 30µL of 5% EDTA (10 µL EDTA/1 mL of blood). After centrifugation at 2500 rpm for 10 minutes at 20° C. the plasma was removed and stored at −20° C. until assay. The total cholesterol was assayed using a standard enzymatic determination kit from Sigma Diagnostics, P. O. Box 14508, St. Louis, Mo. 61378 (Procedure No. 352). The Table that follows shows the effect of droloxifene citrate on total plasma cholesterol. Droloxifene citrate after dosing (5 mg/kg/day for 28 days, po) caused a significant drop (30% versus vehicle treated ovariectomized rats) in total plasma cholesterol.

| Effect of Droloxifene Citrate in Female Rats on Total Plasma Cholesterol | | | |
|---|---|---|---|
| | Plasma Cholesterol (mg/dl) | % Change vs SHAM + VEH | % Change vs OVX + VEH |
| SHAM + VEH | 57 | — | — |
| OVX + VEH | 112 | 96 | — |
| Droloxifene citrate (5 mg/kg/day, 28 days, po) | 78 | +36 | −30 |

The same experiment was performed on Sprague-Dawley male rats (3 month old) sham operated and orchiectomized rats treated with vehicle and droloxifene citrate (10 mg/kg/day for 14 days, po). As shown in the Table below, droloxifene citrate significantly lowered total plasma cholesterol by 48% vs sham operated and 59% vs orchiectomized vehicle treated animals.

| Effect of Droloxifene in Male Rats on Total Plasma Cholesterol | | | |
|---|---|---|---|
| | Plasma Cholesterol (mg/dl) | Change SHAM vs VEH % | Change oophEx + VEH |
| SHAM + VEH | 72 | — | — |
| orchiectomized + VEH | 91 | — | — |
| Droloxifene citrate (10 mg/kg/day, 14 days, po) + VEH | 37 | −48 | −59 |

These data show that droloxifene citrate is effective in treating cardiovascular diseases such as atherosclerosis and hypercholesteremia.

EXAMPLE 3

| Droloxifene Citrate Tablets | |
|---|---|
| Droloxifene citrate | 100 g |
| Lactose | 1190 g |
| Low substituted hydroxypropylcellulose | 250 g |
| Polyvinylpyrrolidone | 50 g |
| Magnesium stearate | 10 g |

The components listed above are mixed together by the usual method, and the mixture thus obtained is compressed into 10,000 tablets each containing 10 mg of droloxifene citrate.

We claim:

1. A method of lowering plasma cholesterol levels, comprising administering to a human in need of treatment of an effective amount of a compound of formula I

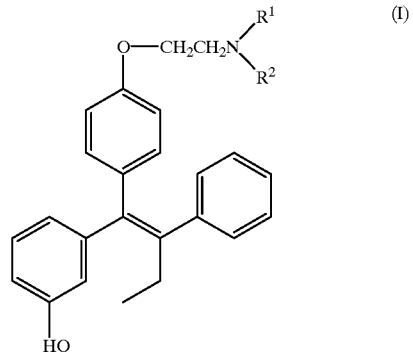

wherein $R^1$ and $R^2$ may be the same of different provided that, when $R^1$ and $R^2$ are the same, each is methyl or ethyl group, and, when $R^1$ and $R^2$ are different, one of them is a methyl or ethyl group and the other is a hydrogen; or a pharmaceutically acceptable salt thereof.

* * * * *